（12）United States Patent
Miyakawa et al.

(10) Patent No.: US 7,396,674 B2
(45) Date of Patent: Jul. 8, 2008

(54) REACTION VESSEL

(75) Inventors: Junji Miyakawa, Ibaraki (JP); Asami Matsumoto, Ibaraki (JP); Shusaku Oka, Ibaraki (JP)

(73) Assignee: Itoham Foods, Inc., Hyogo (JP)

( * ) Notice: Subject to any disclaimer, the term of this patent is extended or adjusted under 35 U.S.C. 154(b) by 0 days.

(21) Appl. No.: 11/690,033

(22) Filed: Mar. 22, 2007

(65) Prior Publication Data
US 2007/0238131 A1    Oct. 11, 2007

Related U.S. Application Data

(63) Continuation of application No. PCT/JP2005/019933, filed on Oct. 28, 2005.

(51) Int. Cl.
*C12M 1/34* (2006.01)
(52) U.S. Cl. .................. 435/287.1; 422/58; 422/59; 422/61; 422/101; 422/102; 435/287.2; 435/288.1; 435/288.2; 435/288.4; 435/288.5; 435/288.6; 435/810; 436/518; 436/810
(58) Field of Classification Search ............ 422/58, 422/59, 61, 101, 102; 435/287.1, 287.2, 435/288.1, 288.2, 288.4, 288.5, 288.6, 810; 436/518, 810
See application file for complete search history.

(56) References Cited

U.S. PATENT DOCUMENTS 3,492,396 A * 1/1970 Dalton et al. ............. 435/7.25
4,254,082 A * 3/1981 Schick et al. .................. 422/55
4,425,438 A * 1/1984 Bauman et al. ............. 436/527

FOREIGN PATENT DOCUMENTS

| JP | 62-011790 | 7/1987 |
|----|-----------|--------|
| JP | 62-169055 | 7/1987 |
| JP | 02-228562 | 9/1990 |
| JP | 06-027111 | 2/1994 |
| JP | 2515392   | 7/1996 |
| WO | WO 03/060479 | 7/2003 |

OTHER PUBLICATIONS

International Search Report issued in PCT/JP2005/019933.

* cited by examiner

*Primary Examiner*—Christopher L Chin
(74) *Attorney, Agent, or Firm*—Marshall, Gerstein & Borun LLP

(57) ABSTRACT

Reaction vessel 1 for assaying of a subject substrate molecule comprises a translucent narrow tube 2 which has a liquid feed port 4 at one end, and which is intended to be packed with microparticles 5 as solid phase support on which a reagent molecule is bound thereto, in which said reagent is capable of binding to, adsorbing, or showing affinity with the subject substrate molecule, and a effluent collecting tube 3 in which a liquid absorbing member 13 is provided inside for absorbing the liquid poured into the narrow tube, and which is connected to the narrow tube 2 at its downstream via a communicating passage 11, and a current-controlling mechanism for controlling liquid current in the narrow tube so as to hold the liquid in the narrow tube 2 during a predetermined time.

13 Claims, 2 Drawing Sheets

REACTION VESSEL

FIELD OF THE INVENTION

The present invention relates to a reaction vessel used for assay, in particular immunoassay method.

BACKGROUND ART

Immunoassay method makes use of antigen-antibody reaction, and is used for detection or quantitative determination of various substrates. This immunoassay method is broadly divided into competitive reaction method, and anti-competitive reaction method. Each method is divided into heterogeneous method which BF-separates antigen-antibody reaction bound form (B: Bound Form) from non-bound free form (F: Free Form), and homogeneous method which does not involve BF separation. The heterogeneous method includes liquid phase method where antigen-antibody reaction proceeds in liquid phase, and solid phase method where it proceeds in the interface between solid phase and liquid phase. For the determination of antigen or antibody, anti-competitive reaction method, in particular heterogeneous-solid phase method such as sandwich method, would apply more often than competitive reaction method since the former shows excellent detection sensitivity.

Exemplary procedures for determining an antigen by sandwich method is as follows: an antibody against an antigen to be determined is bound to a solid-phase support, and thereto is added a test liquid containing the antigen to be determined, to thereby initiate the antigen-antibody reaction (first reaction) in which the antigen specifically binds to the antibody, followed by washing for elimination of contaminants. Then, a labeled substance, for example enzyme-bound enzymatic labeled antibody, is added for initiation of antigen-antibody reaction (second reaction) to thereby bind the enzymatic labeled antibody to the antigen which is bound to the solid-phase support. Subsequently, it is washed for BF separation. For the measurement of enzymatic activity of the enzymatic labeled antibody that was bound to the antigen, a reagent containing a colorimetric substrate or a luminescent substrate is added for initiating enzymatic reaction, and absorbance or luminescence is determined to assay the amount of the antigen.

An example of determination of an antigen by competitive heterogeneous method is as follows: an antibody against an antigen to be determined is bound to a solid-phase support, and thereto are added simultaneously a test liquid containing the antigen to be determined, and a labeled antigen in which a labeled substrate is bound to said antigen, to thereby initiate antigen-antibody reaction for competitive reaction with the antibody in the solid-phase support. In this antigen-antibody reaction, the antigen to be determined and the labeled antigen are bound to the solid-phase support, according to a ratio of respective amount. As in the case of sandwich method, BF separation is then performed to initiate enzymatic reaction. The enzymatic activity in this case depends on an amount of the labeled antigen that was bound, so the amount of the antigen to be determined is determined using calibration curve on the basis of the amount of the labeled antigen added.

Patent document 1 and Patent document 2 describe reaction vessels for use in all of these enzymatic immunoassays. The reaction vessel disclosed in Patent document 1 adopts a structure in which permeable division walls are provided at the upper and lower edges of capillary narrow tubes, and microparticles are packed between these division walls. With binding an antigen or antibody to the microparticles, the narrow tubes are filled with a test liquid to initiate the antigen-antibody reaction. The same applies to the reaction vessel disclosed in Patent document 2 which adopts a structure where microparticles bound to an antigen or antibody are packed in the narrow tubes. Further, in the case of Patent document 2, microparticles are immersed and kept in a preservative solution, while closed-end vent communicates with the narrow tubes at its downstream. The vent is opened upon the assay to thereby enable the passage of the preservative solution and test solution.

Patent document 1: JP Sho62-169,055, A
Patent document 2: JP 2,515,392, B

BRIEF SUMMARY

In the reaction vessels as disclosed in Patent document 1 or Patent document 2, the sample liquid, reagent liquid, or washing liquid to be poured into the narrow tubes upon the assay needs to be drained from the narrow tubes after each completion of the required treatments such as its reaction or washing. In the above-mentioned reaction vessels, these liquids, after drained from the narrow tubes, are collected in a tank outside the reaction vessels with the aim of prevention of secondary pollution. In this case, however, coupling parts such as pipes or ducts are required to be used in order to transfer the liquid to the tank. Further, a pump or aspirator would be needed for aspirating the liquid and generating liquid current, thus complicating the assay instrument. Also, the operation for connecting the coupling parts has been troublesome. Further, pouring of the liquid into the narrow tubes, or its flowing is performed by means of liquid pressure or sucking force through the pump or aspirator, so this has problems of difficult adjustment of liquid current and complicated control.

In accordance with this disclosure, the disclosed reaction vessel does not necessitate the coupling parts for the simplification of the assay instrument by adopting the structure that holds therein a sample liquid, reagent liquid, or washing liquid to be poured into the narrow tube; and permits direct photometry just by its set on the photometric equipment by providing a mechanism for controlling flow velocity of the liquid in the narrow tube; and makes its control easy by omitting a pump.

The disclosed reaction vessel is a reaction vessel for assaying of a subject substrate molecule, comprising: a narrow tube which has a liquid feed port at one end, and which is intended to be packed with microparticles as a solid phase support on which a reagent is molecule bound thereto, in which said reagent molecule is capable of binding to, adsorbing, or showing affinity with the subject substrate molecule; and an effluent collecting tube in which a liquid absorbing member is provided inside for absorbing the liquid poured into the narrow tube, and which is connected to the narrow tube at its downstream via a communicating passage, and further comprising a current-controlling mechanism for controlling liquid current in the narrow tube so as to hold the liquid in the narrow tube during a predetermined time.

In such a reaction vessel, it is preferable that said current-controlling mechanism comprises at least control of liquid sucking force of said liquid absorbing member, and control of flow velocity in said communicating passage. It is also advantageous that said liquid absorbing member comprises a liquid-holding member for holding the absorbed liquid, and an directing member which connects said liquid-holding member to said communicating passage in order to direct to the liquid-holding member the liquid that flows from the communicating passage. Further, it is better that a free space is formed at the upstream of the region where the liquid-holding member is located in said effluent collecting tube. And, it is advantageous that a venting hole is formed at the upstream of the region where the liquid-holding member is located in said effluent collecting tube. Also it is preferable that said venting hole is sealable with a sealing member, or that said liquid feed port is sealable with a sealing member. Further it is better that said liquid absorbing member shows endothermic effect when it absorbs aqueous liquid. Advantageously, the reaction vessel of the present invention is disposable. Preferably, the narrow tube is packed with the solid phase support microparticles. Most advantageously, the reaction vessel of the present invention is used for immunoassay, and the reagent is any one of an antibody or antigen.

According to the disclosed reaction vessel, a sample liquid, washing liquid, labeled antibody liquid, or reaction reagent such as luminescent substrate, colorimetric substrate, or fluorescent substrate is poured into a narrow tube that is packed with solid phase support microparticles under various assays methods, thereby inducing luminescence or coloration inside the narrow tube that is packed with solid phase support microparticles. Therefore, measurement of its coloration amount, absorption of light, fluorescence intensity, etc, allows a substance to be identified or determined in the sample liquid.

The disclosed reaction vessel adopts the structure in which the liquid absorbing member absorbs the liquid being poured into the narrow tube, and thus collects it within the effluent collecting tube to prevent second pollution. Therefore, it is not necessary to build a tank outside the reaction vessel with the aim of prevention of secondary pollution. In addition to the tank, coupling parts for connecting the tank or photometric equipment to the reaction vessel would be unnecessary. Thus it is possible to adopt a simple structure, and also connecting operation for prevention of second pollution would be unnecessary, thereby enabling the measurement to be easily performed.

Also, the disclosed reaction vessel controls liquid current in the narrow tube by means of current-controlling mechanism, so that the adjustment of the sucking force is unnecessary, thereby facilitating the control. Additionally, any exterior sucking means such as a pump or means for controlling the current to the photometric equipment would be unnecessary, thus allows adoption of further simple structure.

EXPLANATION OF LETTERS OR NUMERALS

Figure 1:
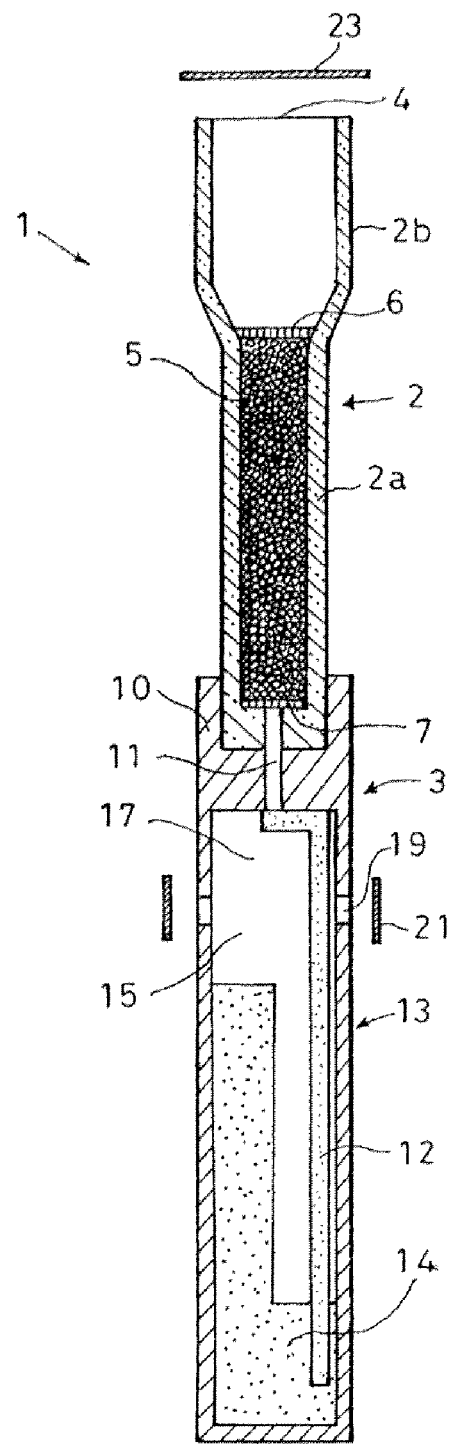
FIG. 1 is a cross-sectional view showing an example of the reaction vessel according to the first embodiment of the present invention.

A listing of the reference numerals used in the application is provided below. The list is provided for convenience purposes and not by way of limitation. It will be understood that the application describes example embodiments, but that the application (in particular the claims) is not limited to the embodiments bearing these reference numerals. Further it will be appreciate that the figures illustrate features in addition to those recited with reference numerals listed below. Furthermore, any similar wording used in the claims is not limited to the particular corresponding structure shown in the drawings and listed below.
1. Reaction Vessel
2. Narrow Tube
3. Effluent collecting tube
4. Liquid feed port
5. Solid Phase Support Microparticles
6, 7. Division wall
11. Communicating Passage
12. Directing Member
13. Liquid Absorbing Member
14. Liquid Holding Member
15. Space
17. Free Space
19. Venting Hole
21,23. Sealing member

DETAILED DISCLOSURE

Now, the best mode for working the reaction vessel according to the invention is explained in detail with reference to the drawings. In each embodiment, the same number is attached to the same member for ease of reference.

FIG. 1 shows reaction vessel 1 according to the first embodiment of the present invention, which is equipped with narrow tube 2, and effluent collecting tube 3, and which includes current-controlling mechanism. This reaction vessel 1 is used for immunoassay, and is disposable, and can be put on the shelf by being directly subject to autoclave procedure or incineration, etc. after use in immunoassay. Immunoassay methods which are applicable to the reaction vessel 1 according to this embodiment, can include any methods provided that they can determine an antigen (including hapten antigen) or antibody to be measured, qualitatively, or quantitatively, or semiquantitatively be means of immune reaction. The immunoassay methods can specifically include, EIA: Enzyme Immunoassay such as ELISA: Enzyme-linked Immunosorbent Assay, FEIA: Fluorescent Enzyme Immunoassay, CLEIA: Chemiluminescent Enzyme Immunoassay, BLEIA: Bioluminescent Enzyme Immunoassay; or without any enzyme, FIA: Fluorescent Immunoassay, CLIA: Chemiluminescent Immunoassay, BLIA: Bioluminescent Immunoassay for example.

However, the disclosed reaction vessel is used not only for immunoassay, but also for any of the other assay methods, provided that these assay methods makes use of the binding, adsorption, and/or affinity property between two kinds of molecules. These relationships could occur in the organism, and can include, for example, ligand/receptor, hormone/receptor, virus/receptor, nucleic acid-binding peptide or protein/nucleic acid, enzyme/substrate, and the other reactions between biologic molecules showing high absorptivity and/or affinity (pair of peptides or proteins, peptide or protein and nucleic acid, sugar and peptide or protein, phospholipid and peptide or protein), as well as antigen/antibody. Further, the above-mentioned relationships based on the binding, adsorption, and/or affinity property could be in vitro, or in vivo; and may occur between macro molecules, or macro molecule and low molecule.

In narrow tube 2, enzymatic reaction proceeds, and light and color which occur upon the enzymatic reaction is measured. This narrow tube 2 is formed of main body part 2a as enzymatic reaction site and measurement site, and liquid feed part 2b which is integrally provided at one end (upper end) of main body part 2a. The whole is made of translucent material such as translucent or half-translucent glass tube, resinous tube, etc. Thus the whole of narrow tube 2 is made of translucent material, so it is possible to determine the degree of luminescence or coloration through main body part 2a. Liquid feed part 2b is formed so that it is rather larger in diameter than main body part 2a, and its one end (upper end) is opened to constitute liquid feed port 4. Liquid such as sample liquid or washing liquid is poured from liquid feed port 4, and the liquid poured flows down from liquid feed part 2b to main body part 2a.

The inside diameter or length of liquid feed part 2b and the inside diameter or length of main body part 2a is properly modified according to the amount and viscosity of the liquid to be determined, method for determination, etc. In case that it is employed in ELISA method, liquid feed part 2b is adjusted, for example, to an inner diameter of about 5-7 mm and a length of about 10-15 mm, and main body part 2a is adjusted, for example, to an inside diameter of about 2.5-3.0 mm and a length of about 25-30 mm.

The inside of main body part 2a is filled with solid phase support microparticles 5. In this case, preamble division walls 6, 7 are provided at both the longitudinal ends (upper and lower ends) inside main body part 2a, and solid phase support microparticles 5 are packed between these division walls 6, 7. Division wall 6, 7 can be made of any preamble material such as preamble membrane filter material, or glass wool filter material. Such packing can prevent solid phase support microparticles 5 from leaking out of narrow tube 2. Further, division wall 7 can function as one member that constitutes the current-controlling mechanism, through the adjustment of its thickness, pore size, etc.

Solid phase support microparticles 5 perform an assay reaction with a subject substrate in sample liquid, and include a reagent as being bound thereto. The regent should be capable of binding to, adsorbing, or showing affinity with the subject substrate. In case the assay reaction is immune reaction, solid phase support microparticles 5 include one of antibody or antigen as being bound thereto. Thus, in case an antigen is to be measured, an antibody to be reacted with the antigen is bound thereto. In case an antibody is to be measured, an antigen that corresponds to the antibody is bound thereto. Within the framework of the present invention, hapten is also referred to as the antigen. As microparticles for solid phase support microparticles 5, glass beads or polystyrene beads can be advantageously employed, and porous beads (porous support) can be also used. The average particle diameter of these microparticles is adjusted so that the surface area of the total amount packed in main body part 2a becomes as large as possible, and is adjusted appropriately, for example, within the range of 100-250 μm in diameter. The binding of an antibody or antigen to such microparticles can be conducted using conventional immunoassay methods such as physical adsorption or covalent binding.

For the binding of an antibody or antigen, surface treatment of microparticles may be performed in advance. When the microparticles are glass beads for example, this surface treatment can be performed by washing them with pure water or alcohol, drying, treating them with ultrasonic in an organic solution of silanes for silylation treatment, and then washing. Also, amino group-silane treatment, or carboxyl treatment is also possible in addition to, or instead of the silane silylation. After such surface treatment, an antigen or antibody is bound thereto, and is subject to blocking treatment for use in immunoassay method. The blocking treatment may rely on any blocking agents or any blocking treatment methods provided that nonspecific adsorption by the other proteins or polypeptides than the object antigen or antibody can be prevented. For example, albumin, skim milk, gelatin, casein, as well as commercial blocking agents can be used.

Effluent collecting tube 3 is concentrically connected to the end (lower end) on the opposite side to liquid feed port 4 in main body part 2a. Effluent collecting tube 3 contains linking port 10 which fits to the lower end of main body part 2a from the outside, and the fit of this linking port 10 to main body part 2a connects effluent collecting tube 3 to narrow tube 2. The connected effluent collecting tube 3, coupled with narrow tube 2, is subjected to treatment or operation from initiation of the determination to disposal after termination of the determination.

Effluent collecting tube 3 is molded into a bottom-having tubular form from glass, resin, etc. This effluent collecting tube 3 absorbs and collects the liquid being poured into narrow tube 2. To this end, effluent collecting tube 3 and narrow tube 2 communicates with each other so that the liquid is transferred into effluent collecting tube 3. This communication is completed through the formation of a through-hole at almost central portion of the bottom face of narrow tube 2, and also the formation of another through-hole that corresponds to the former through-hole at the upper end of effluent collecting tube 3. These through-holes are formed to have the same diameter, and communication of the through-hole of narrow tube 2 with the through-hole of effluent collecting tube 3 forms communicating passage 11.

Vertically long space 15 is formed within effluent collecting tube 3, and liquid absorbing member 13 which aspirates the liquid being poured into narrow tube 2, is provided in this space. In this embodiment, liquid absorbing member 13 is composed of liquid holding member 14 which is supported at the bottom side of space 15, and directing member 12 which connects liquid holding member 14 to the above-mentioned communicating passage 11. These liquid holding member 14 and directing member 12 can be made of material that can aspirate liquid by capillary force and hold it, for example fabric, nonwoven fabric, fibrous paper material. Such material for the liquid holding member 14 and directing member 12 can include natural material such as paper material or silk cotton material, and also high water-absorption resinous material which swells by absorbing liquid, and which is made of hydrophilic resin such as polyvinyl alcohol based, salt of polyacrylate based, vinyl acetate-salt of polyacrylate based, starch-acrylic acid graft based. Further, it can be composed of combined material of plural kinds of such high water-absorption resinous material, or combined material of high water-absorption resinous material with natural material. As the high water-absorption resinous material, there can be employed a crosslinked form, a porous form, a porous crosslinked form of the above-mentioned hydrophilic resin.

The size, etc. of liquid holding member 14 is adjusted so that it shows absorbing ability which allows it to absorb and hold the total liquid such as sample liquid or washing liquid being poured into narrow tube 2 for determination. Thus liquid holding member 14 holds the total liquid used in the determination, so the liquid is sealed inside effluent collecting tube 3 to thereby enable prevention of secondary pollution and improves the safety dramatically.

Directing member 12 is extended in space 15 toward the long direction while the upper end thereof stays in contact with the lower surface portion of communicating passage 11. By inserting the lower end thereof into liquid holding member 14, it acts as absorbing the liquid from communicating passage 11, and directing it to liquid holding member 14.

Effluent collecting tube 3 is required not to generate any noise through leakage of light, etc. when luminescence such as chemical luminescence or biological luminescence is determined in narrow tube 2. Therefore effluent collecting tube 3 is constituted so as to show light blocking effect. To this end, it is preferable that the whole of effluent collecting tube 3 is blacked, or that the surround of effluent collecting tube 3 is covered with a shading sheet. In reaction vessel 1 of this embodiment, it is possible to determine absorbance or fluorescence intensity of the liquid in communicating passage 11, not the determination of luminescence in main body part 2a of narrow tube 2. In this case, effluent collecting tube 3 is required to have translucency; hence, translucent material is employed for effluent collecting tube 3. Thus, concerning effluent collecting tube 3, shading material or translucent material is selected according to the embodiment of determination.

In this embodiment, free space 17 is provided above space 15 where liquid holding member 14 is set. Free space 17 is provided above space 15, to thereby locate at the upstream of the region where liquid holding member 14 is located. Even if the liquid overflows liquid holding member 14 for reasons of much amount of the liquid employed, such structure enables the holding of the liquid within effluent collecting tube 3 because free space 17 is provided at the upstream of liquid holding member 14; and thus improves the safeness. Further, liquid holding member 14 can be made of material comprising high water-absorption resinous material which swells by absorption of the liquid and holds water at a weight ratio of several times or over, to thereby secure free space 17 the volume which accommodates the swelling of liquid holding member 14.

Thus, the structure where effluent collecting tube 3 is connected to narrow tube 2 and thus the liquid is collected for pooling in effluent collecting tube 3 would not require a tank for preventing second pollution, which is to be provided outside reaction vessel 1. In addition to the tank, coupling parts for connecting the tank to the reaction vessel becomes unnecessary. Thus it would be possible to adopt a simple structure, thereby enabling determination to be easily performed.

Venting hole 19 is formed at the side of effluent collecting tube 3. Venting hole 19 is intended to keep the pressure inside effluent collecting tube 3 at normal pressure, and thus allows the liquid to free-flow within communicating passage 11. Venting hole 19 is formed to locate above liquid holding member 14, i.e. at the upstream of liquid holding member 14, and thus can prevent the liquid, which overflows liquid holding member 14, from leaking outside from venting hole 19.

Current-controlling mechanism controls liquid current in narrow tube 2 and adjusts so as to hold the liquid in narrow tube 2 during a predetermined time. By holding the liquid in narrow tube 2 during a predetermined time in such a way, enzymatic reaction and luminous/chromogenic reaction can be assured, highly accurate determination becomes possible.

Specific members for current-controlling mechanism are involved in the above-mentioned communicating passage 11 or liquid absorbing member 13, in particular directing member 12. For example, the diameter or length of communicating passage 11 may be modified according to the viscosity of the liquid, etc. to control flow velocity in communicating passage 11. Alternatively, the sucking force of liquid absorbing member 13 may be controlled, or the combination of these may control liquid current. By providing current-controlling mechanism to control flow velocity in narrow tube 2 in such a way, exterior adjustment of the sucking force would be unnecessary, thereby facilitating the control. Additionally, any exterior sucking means such as a tank would be unnecessary, and thus allows adoption of simple structure.

As the above-mentioned liquid absorbing member 13 comprising directing member 12, and liquid holding member 14, employed is material showing endothermic effect when it absorbs aqueous liquid. This material can include absorbent fiber containing xylitol, erythritol, etc. Further, liquid absorbing member 13 may be constituted to hold therein potassium nitrate, potassium chloride, ammonium nitrate, urea, which realizes absorption of heat when it absorbs aqueous liquid.

Since liquid absorbing member 13 absorbs the heat upon the absorption of aqueous liquid in such a way, space 15 in effluent collecting tube 3 is put under reduced pressure, so the liquid in narrow tube 2 can be absorbed smoothly by liquid absorbing member 13 via communicating passage 11. Thus liquid absorbing member 13 shows endothermic effect, which changes flow velocity in communicating passage 11; hence, liquid absorbing member 13 showing endothermic effect could function as current-controlling mechanism.

The above-mentioned venting hole 19 can be sealed by attaching sealing member 21 to effluent collecting tube 3 around venting hole 19. Sealing member 21 seals venting hole 19 with adhesive, and detachment and reattachment are possible appropriately. Upon the determination, therefore, detachment of sealing member 21 put the inside of effluent collecting tube 3 under normal pressure, and it becomes possible to seal venting hole 19 with sealing material 21 after collecting the liquid used in the determination. This prevents the liquid from flowing out via venting hole 19 upon the disposal of reaction vessel 1, thus prevents second pollution and further improves the safeness.

This applies to liquid feed port 4 of narrow tube 2, and sealing member 23 can be employed which seals liquid feed port 4 and allows the detachment and reattachment. And, upon the determination, detachment of sealing member 23 allows the liquid to be poured from liquid feed port 4. Sealing of liquid feed port 4 with sealing member 23 after finishing the determination prevents the liquid from flowing out via liquid feed port 4 upon the disposal of reaction vessel 1, and can improve the safeness.

Figure 2:
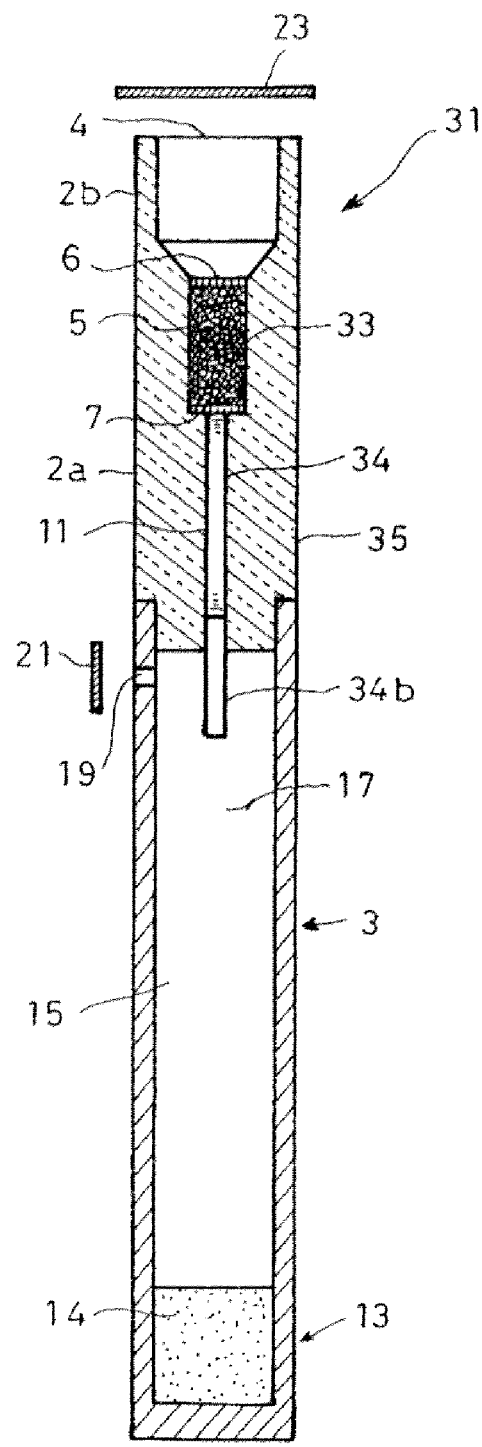
FIG. 2 is a cross-sectional view showing an example of the reaction vessel according to the second embodiment of the present invention.

FIG. 2 shows reaction vessel 31 according to the second embodiment. This embodiment also includes narrow tube 2, and effluent collecting tube 3 which is connected to the lower end of narrow tube 2, and current-controlling mechanism. In this case, narrow tube 2 and effluent collecting tube 3 are approximately the same in outer diameter, and they do not have unevenness on the external surface, so the handleability and self life are improved.

Narrow tube 2 is composed of main body part 2a as enzymatic reaction site and measurement site, and liquid feed part 2b that is provided on the upper end of main body part 2a in an integrated fashion, and the whole is formed out of translucent material. Microparticles collecting station 33 is formed above main body part 2a of narrow tube 2, and this microparticles collecting station 33 is packed with solid phase support microparticles 5 which is similar to the first embodiment. At the upper and lower ends of microparticles collecting station 33, provided are preamble division walls 6, 7 which are similar to the first embodiment, so solid phase support microparticles 5 are prevented from leaking out of narrow tube 2.

In main body part 2a of narrow tube 2, sub-measurement site 35 is formed in an integrated fashion and is extended so that it is longer below microparticles collecting station 33. Translucent draining tube 34 is inserted into this sub-measurement site 35. Draining tube 34 is inserted into sub-measurement site 35 from the below, and thus this upper end is in contact with division wall 7, so draining tube 34 communicates with microparticles collecting station 33. This communication allows the liquid to flow into draining tube 34 after passing through microparticles collecting station 33.

According to this embodiment, luminescence and coloration by enzymatic reaction can be measured in microparticles collecting station 33 (i.e. main body part 2a) which is packed with solid phase support microparticles 5. Additionally, sub measurement site 35 becomes longer and draining tube 34 is inserted into this sub measurement site 35, so it becomes possible to measure at sub measurement site 35 the degree of coloration of the liquid within the draining tube.

Draining tube 34 is provided extendedly so as to be exposed below the lower end of main body part 2a, and this extended part 34b is inserted into space 15 of effluent collecting tube 3. Thus draining tube 34 constitutes communicating passage 11 which directs the liquid being poured into narrow tube 2, to effluent collecting tube 3.

Liquid holding member 14 is provided inside effluent collecting tube 3. Liquid holding member 14 is provided to locate on the bottom of effluent collecting tube 3, and absorbs and holds the liquid which flows down from draining tube 34. The size, etc. of liquid holding member 14 is adjusted so that it shows absorbing ability which allows it to hold the total liquid being poured into narrow tube 2 as in the case of the first embodiment. Therefore, the total liquid used in the measurement can be sealed inside effluent collecting tube 3, so second pollution can be prevented and the safeness is improved. According to this embodiment, directing member 12 in the first embodiment is not provided, only liquid holding member 14 constitutes liquid absorbing member 13.

According to this embodiment, space 15 above liquid holding member 14 is vertically long, so the part above space 15 constitutes free space 17. Therefore, it becomes possible to hold the liquid inside effluent collecting tube 3 even if the liquid flows out of liquid holding member 14 for the large quantity of the liquid used in the measurement.

According to this embodiment as well, the current-controlling mechanism control liquid current so as to hold the liquid in narrow tube 2 during a predetermined time after pouring it into narrow tube 2. The current-controlling mechanism according to this embodiment is constituted by adjusting the inner diameter or length of microparticles collecting station 33, the diameter or packing density of solid phase support microparticles 5, the thickness or pore size of division wall 7, etc. Further, when a member showing endothermic effect when it absorbs aqueous liquid is employed as liquid holding member 14, liquid holding member 14 also functions as the current-controlling mechanism.

According to this embodiment, venting hole 19 is formed at the side of effluent collecting tube 3 above space 15. Further, sealing member 21 is attached to venting hole 19 detachably and readherably (reattachably). Sealing member 23 is attached to liquid feed port 4 of narrow tube 2 detachably and readherably.

The exemplary size of reaction vessel 31 according to this embodiment is explained. The diameter of reaction vessel 31 can be set to 7-10 mm, the length thereof to 70-100 mm, the inner diameter of microparticles collecting station 33 to 2-3 mm, the length thereof to 10 mm, the inner diameter of draining tube 34 to 1-1.5 mm, and the length to 14 mm. Further the length of effluent collecting tube 3 can be set to 40-50 mm, with the volume thereof being 1.0-1.5 mL.

According to such embodiment, the liquid pools in effluent collecting tube 3 after poured into narrow tube 2, leading to the prevention of second pollution as in the case of the first embodiment. Further the provision of the current-controlling mechanism controls liquid current in narrow tube 2, so that the adjustment of liquid sucking force would be unnecessary, and simple structure could be adopted. Concerning this second embodiment, however, redundant explanation is omitted about the parts similar to the first embodiment, including the kind of assay method applicable to reaction vessel 31, or the material, structure, form of each member.

INDUSTRIAL APPLICABILITY

The disclosed reaction vessel is applicable to any assay methods which makes use of the binding, adsorption, and/or affinity property between two kinds of molecules, in particular any immunoassay methods such as Enzyme Immunoassay (EIA) such as Enzyme-linked Immunosorbent Assay (ELISA), Fluorescent Enzyme Immunoassay (FEIA), Chemiluminescent Enzyme Immunoassay (CLEIA), Bioluminescent Enzyme Immunoassay (BLEIA); or without any enzyme, Fluorescent Immunoassay (FIA), Chemiluminescent Immunoassay (CLIA), Bioluminescent Immunoassay (BLIA). By pouring sample liquid, washing liquid, or reaction reagent in accordance with various assay methods, it is possible to directly measure coloration amount, absorption of light, fluorescence intensity, etc. in the narrow tube that is packed with solid phase support microparticles, and the identification or determination of a substance in sample liquid can be easily conducted for a short time with high sensitivity. Further, the disclosed reaction vessel has a structure where the liquid is absorbed by a liquid absorbing member after poured into a narrow tube, and thus pools in an effluent collecting tube, and prevents second pollution; hence, it is not necessary for a tack to be provided additionally outside the reaction vessel. Any coupling parts for connecting photometric equipment to the reaction vessel would be unnecessary, and a simple structure can be adopted. The connecting operation for prevention of second pollution would be unnecessary, thereby enabling measurement to be easily performed. Also, the disclosed reaction vessel has current-controlling mechanism and controls the liquid current in the narrow tube, so that the adjustment of the sucking force is unnecessary and the control becomes easy, and any exterior sucking means such as a pump, or means for controlling the current into the photometric equipment would be unnecessary. Furthermore, the reaction vessel, after used in assay, can be put on the shelf by being directly subject to autoclave procedure or incineration, etc., and is useful in view of management for safety and health for handlers.

By adopting the structure which holds therein a liquid such as a sample liquid, reagent liquid, or washing reagent, any connection members would be unnecessary for simplification; and the provision of a function of regulating the flow velocity in a narrow tube, can eliminate the need to provide any pump and can facilitate the control.

The invention claimed is:

1. A reaction vessel for assaying of a subject substrate molecule, comprising a narrow tube which has a liquid feed port at one end, and which is intended to be packed with microparticles as a solid phase support on which a reagent molecule is bound thereto, in which said reagent molecule is capable of binding to, adsorbing, or showing affinity with the subject substrate molecule, and a effluent collecting tube in which a liquid absorbing member is provided inside for absorbing the liquid poured into the narrow tube, and which is connected to the narrow tube at its downstream via a communicating passage, and further comprising a current-controlling mechanism for controlling liquid current in the narrow tube so as to hold the liquid in the narrow tube during a predetermined time.

2. The reaction vessel according to claim 1, wherein said current-controlling mechanism comprises at least control of liquid sucking force of said liquid absorbing member, and control of flow velocity in said communicating passage.

3. The reaction vessel according to claim 1, wherein said liquid absorbing member comprises a liquid-holding member for holding the absorbed liquid, and a directing member which connects said liquid-holding member to said communicating passage in order to direct to the liquid-holding member the liquid that flows from the communicating passage.

4. The reaction vessel according to claim 3, wherein a free space is formed upstream of the region where the liquid-holding member is located in said effluent collecting tube.

5. The reaction vessel according to claim 3, wherein a venting hole is formed upstream of the region where the liquid-holding member is located in said effluent collecting tube.

6. The reaction vessel according to claim 5, wherein said venting hole is sealable with a sealing member.

7. The reaction vessel according to claim 1, wherein said liquid feed port is sealable with a sealing member.

8. The reaction vessel according to claim 1, wherein said liquid absorbing member shows endothermic effect when it absorbs aqueous liquid.

9. The reaction vessel according to claim 1, wherein the microparticles are glass beads.

10. The reaction vessel according to claim 1, wherein the microparticles are porous beads.

11. The reaction vessel according to claim 1, wherein said reaction vessel is disposable.

12. The reaction vessel according to claim 1, wherein the narrow tube is packed with the microparticles.

13. The reaction vessel according to claim 1, wherein said reaction vessel is used for immunoassay, and the reagent molecule is any one of an antibody or antigen.

* * * * *